United States Patent
Bhatia

(10) Patent No.: US 6,818,781 B2
(45) Date of Patent: Nov. 16, 2004

(54) SIMULTANEOUS REACTION AND SEPARATION PROCESS FOR THE MANUFACTURE OF DIANHYDRO SUGAR ALCOHOLS

(75) Inventor: Kamlesh Kumar Bhatia, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/414,611

(22) Filed: Apr. 16, 2003

(65) Prior Publication Data

US 2004/0030162 A1 Feb. 12, 2004

Related U.S. Application Data

(60) Provisional application No. 60/373,106, filed on Apr. 17, 2002.

(51) Int. Cl.$^7$ .............................................. C07D 307/93
(52) U.S. Cl. ....................................................... 549/465
(58) Field of Search .......................................... 549/465

(56) References Cited

U.S. PATENT DOCUMENTS

| | | |
|---|---|---|
| 4,313,884 A | 2/1982 | Arena |
| 4,506,086 A * | 3/1985 | Salzburg et al. ............ 549/464 |
| 4,564,692 A * | 1/1986 | Feldmann et al. .......... 549/464 |
| 4,861,513 A * | 8/1989 | Lueders et al. ........ 252/182.24 |
| 5,306,831 A * | 4/1994 | Beshouri et al. ............ 549/478 |
| 6,407,266 B2 | 6/2002 | Bhatia |

FOREIGN PATENT DOCUMENTS

| | | | |
|---|---|---|---|
| WO | WO 00/14081 | * | 3/2000 |
| WO | WO 01/92246 | | 6/2001 |

OTHER PUBLICATIONS

International Search Report for PCT/US03/11998 dated Oct. 30, 2003.
Przem. Chem. 48(11) pp. 655–668, 1969.
G. Fleche and M. Huchette, Isosorbide, Preparation, Properties and Chemistry, 36th Starch Convention of the Arbeitsgemeinschaft Getreideforschung, (1986), 38(c), 26–30.
K. Bock, C. Pedersen and H. Thogersen, Acid Catalyzed Dehydration of Alditols. Part I. D–Glucitol and D–Mannitol, Acta Chemica. Scandinavica, B 35, 441–449, 1981.
U.S. Provisional patent application Ser. No. 60/246,038, filed Nov. 6, 2000.

* cited by examiner

Primary Examiner—Amelia A. Owens

(57) ABSTRACT

A continuous process for the manufacture of dianhydro sugar alcohols by dehydration of the corresponding sugar alcohols or monoanhydro sugar alcohols in the presence of a dehydration catalyst, using evolved water vapor as a carrier for continuous separation of the product from the reaction mass.

20 Claims, 1 Drawing Sheet

SIMULTANEOUS REACTION AND SEPARATION PROCESS FOR THE MANUFACTURE OF DIANHYDRO SUGAR ALCOHOLS

FIELD OF THE INVENTION

This invention concerns a continuous process for the manufacture of dianhydro sugar alcohols by the dehydration of the corresponding sugar alcohols in the presence of a dehydration catalyst, using evolved water vapor as a carrier for continuous separation of the product from the reaction mass.

TECHNICAL BACKGROUND OF THE INVENTION

Anhydro sugar alcohols, in particular derivatives of mannitol, iditol, and sorbitol, are known for their therapeutic uses and uses in food. At least one of these, isosorbide, 1,4:3,6-dianhydrosorbitol, is useful as a monomer used in the manufacture of polymers and copolymers, especially polyester polymers and copolymers.

Anhydro sugar alcohols are produced by dehydration of the corresponding sugar alcohols (or monoanhydro sugar alcohols) by the action of various dehydration catalysts, typically strong acid catalysts such as sulfonated polystyrenes (H+ form) and various mineral acids (e.g., HCl, $H_3PO_4$, HF, $H_2SO_4$). Batch processes for the preparation of dianhydro sugar alcohols by acid dehydration are known in the art.

It is known that the dehydration of sorbitol to isosorbide proceeds at a very slow rate if water is not removed effectively from the reaction mass. G. Flèche and M. Huchette, *Starch/Starke* (1986), 38(c), 26–30, have shown that at 135° C., the reaction may take as long as 10 to 15 hours to complete if carried out at atmospheric pressure, but with removal of water under vacuum, the reaction time is reduced to 2 to 3 hours. Organic solvents such as xylene and toluene have also been employed to facilitate the removal of water (*Przem. Chem.* 48(11) pp. 665–668 (1969)).

A batch process for the formation of the dianhydro sugar alcohol isosorbide has been described as a two step process involving intramolecular dehydration of sorbitol to sorbitan (1,4-monoanhydrosorbitol), and further reaction of sorbitan to isosorbide (1,4:3,6-dianhydrosorbitol) in an acid catalyzed dehydration-cyclization. In this process, an aqueous solution of sorbitol is charged to a batch reactor. The temperature is increased to 130 6C.–135° C. under vacuum (35 mm Hg) to remove the water. When most of the free water has been removed, a catalyst, usually sulfuric acid, is added and the temperature and vacuum levels are maintained. The operable temperature range of the reaction is narrow. Higher temperatures lead to decomposition and charring of the end product, while lower temperatures reduce the reaction rate and make it difficult to remove the water of reaction. This reaction produces isosorbide and a higher molecular weight by-product. The by-product is presumably produced by water elimination between two or more sorbitol molecules, but its exact nature is not clearly defined. See G. Flèche and M. Huchette, *Starch/Starke* (1986), 38(c), 26≧30 and Roland Beck, *Pharm. Mfg Inc.* (1996), 97–100. Other monoanhydro by-products, 2,5-anhydro-L-iditol and 2,5-anhydro-D-mannitol, are also known to be produced under some reaction conditions (K. Bock et al., *Acta. Chem. Scand. B* 35, 441–449 (1981)).

For isosorbide to be used as a monomer in high volume polymers and copolymers, it needs to be produced in large quantities, preferably in a continuous process.

WO 00/14081 describes a continuous process for producing anhydro sugar alcohols, especially isosorbide, comprising the steps of introducing at least one sugar alcohol or monoanhydro sugar alcohol into a reaction vessel; dehydrating the sugar alcohol or monoanhydro sugar alcohol in the presence of an acid catalyst and an organic solvent to form a reaction product which is at least partly soluble in the organic solvent; removing water from the reaction vessel; removing organic solvent comprising the dissolved reaction product from the reaction vessel; separating the reaction product from the removed organic solvent; and recycling the organic solvent into the reaction vessel.

U.S. Pat. No. 6,407,266 describes a continuous process in which a process stream containing at least one sugar alcohol or monoanhydro sugar alcohol and, optionally, water is introduced to the first stage of a multistage reactor and then intimately contacted with a countercurrent flow of an inert gas at elevated temperature. This inert gas removes the bulk of any water present in the process stream. This dewatered process stream is then intimately contacted, in the presence of a dehydration catalyst, with a counter current flow of an inert gas at elevated temperatures to remove water of reaction as formed. Finally, the product is removed from the bottom of the reactor.

The reaction product obtained by processes such as the above contains about 70 to 80% isosorbide and about 20 to 30% undesired reaction byproducts. The reaction product thus needs to be subjected to one or more separation steps, such as evaporation, distillation or chromatographic separation, to isolate the isosorbide. Chromatographic separation is disclosed in U.S. patent application Ser. No. 60/246038. Separation by vaporization or distillation is difficult because of the low vapor pressure of isosorbide. At 140° C., the vapor pressure of isosorbide is only 1.75 mm Hg. Evaporation or distillation at temperatures of about 140° C. is desirable to minimize product degradation and obtain good purity isosorbide, but the recovery is poor. At higher temperatures, e.g., 170° C., more isosorbide is recovered, but it is of poorer quality.

The sorbitol used in such processes is typically manufactured as an aqueous solution containing about 50% by weight of sorbitol. This "raw" solution is then concentrated by evaporation by the manufacturer, typically to about 70% by weight sorbitol. It is this concentrated solution that is used in the above-described processes for making isosorbide. A process that could effectively use the original, more dilute solution would thus be more economical, since the evaporative step would not be necessary.

It is the object of the present invention to provide an economically attractive, continuous process wherein the feed sugar alcohols may be a dilute aqueous solution, the reaction and separation occur simultaneously in a single multistage reactor, and the free water plus the water of reaction evolved are used to facilitate separation.

SUMMARY OF THE INVENTION

In accordance with the object of this invention, there is provided a continuous process for the manufacture of dianhydro sugar alcohols comprising:

a) continuously feeding an aqueous solution comprising one or more sugar alcohols or monoanhydro sugar alcohols to a first stage of a multistage reaction vessel;

b) continuously heating the aqueous solution in the first stage in the presence of a dehydration catalyst to form a partially dehydrated reaction mass and water vapor;

c) simultaneously transporting the partially dehydrated reaction mass from the first stage upwards to one or more additional stages of the multistage reactor with water vapor from step (b) while further dehydrating the sugar alcohols to form dianhydro sugar alcohols and simultaneously removing from the reaction mass most of the dianhydro sugar alcohols formed;

d) continuously removing a vapor stream comprising water and dianhydro sugar alcohol product from the reaction vessel and recovering the dianhydro sugar alcohols; and e) continuously removing high boiling by-products from the reaction vessel as a liquid stream from the final stage of the reaction vessel at a rate coordinated with the feed rate of the aqueous solution so as to maintain a nearly constant quantity of reaction mass in the multistage reaction vessel.

DETAILED DESCRIPTION OF THE INVENTION

Figure 1:
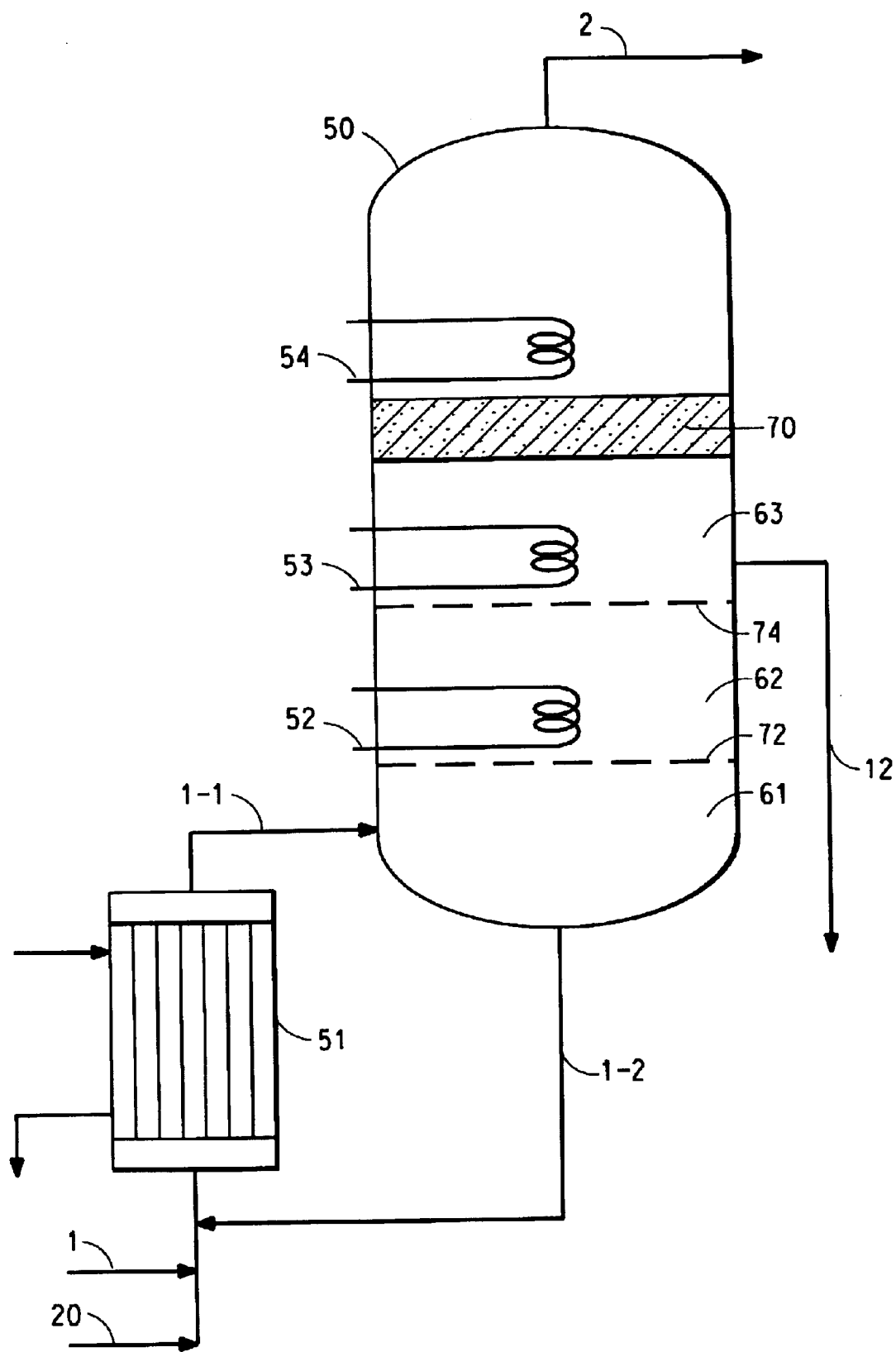
FIG. 1 is a schematic representation of a preferred process of the present invention.

The present disclosure describes a process for the production of dianhydro sugar alcohols from the corresponding sugar alcohols or monoanhydro sugar alcohols.

In the process of the present invention, the dehydration reaction that produces the dianhydro sugar alcohols and the separation of the product from the reaction mass are carried out at the same time. This is achieved by continuously feeding to the reaction vessel a "dilute" (preferably about 45–50 wt %) aqueous solution of sugar alcohols, and using the evolved water vapor to mix and agitate the reaction mass, and also to assist in removing the dianhydro sugar alcohols formed. The reaction vessel is compartmentalized into two or more stages, such that the reaction occurs as if it were being done in a number of well-mixed reactors in series. This reduces the residence time required to complete the reaction, and the reaction mass is not subjected to long periods at elevated temperature. Furthermore, the reaction mass is transported from one stage to the next by the water vapor itself.

The process of the present invention is thus directed toward the production of anhydro sugar alcohols and generally includes the steps of introducing an aqueous solution of at least one sugar alcohol, preferably at about 45–50% by weight, to a multistage reaction vessel; evaporating most of the water from this aqueous solution and dehydrating the sugar alcohols in the presence of a catalyst to form anhydro sugar alcohols and additional water vapor; transporting the reaction mass through the stages with the vapors evolved; and removing the anhydro sugar alcohol product along with the water vapor from the top of the reactor for subsequent use or further purification. The high boiling byproducts are removed from the reactor as a liquid stream. Further, the process is continuous in that the steps of introducing the sugar alcohol(s), removing the product vapor stream, and removing the high boiling byproducts occur simultaneously, and their rates are coordinated to maintain a steady amount of reaction mass in the reactor.

The product can be recovered from the vapor stream by condensation and optionally subjected to one or more purification steps, such as ion exchange, solution or melt crystallization, activated carbon treatment, or combinations thereof. Purification of the product can be carried out as part of the continuous process or in a separate process. The high boiling byproducts stream can be put to other uses or disposed of in a safe manner. Useful species present therein may be recovered. For example, unrecovered anhydro sugar alcohols present in the stream can be recovered in a wiped film evaporator.

The reaction vessel can be maintained at the desired elevated temperature by any suitable means, such as including internal heating coils in each stage or circulating the reaction mass through an external heat exchanger. Separate heat input for each stage allows temperature control at each stage and operation at an optimum temperature profile. An external heat exchanger is preferred for the first stage for ease of fabrication, particularly at large scale, to handle the large heat load required for evaporating most of the excess water at that stage.

The reaction vessel is compartmentalized with sieve trays to obtain multiple stages. The hole size and open area of the sieve trays are designed such that, at the vapor velocities for which the reactor is designed, the vapor stream can carry the reaction mass by entrainment through the sieve trays from one stage to the stage above with minimal leakage ("weeping") back to the stage below. The reaction vessel is designed for a vapor velocity that is high enough to provide good agitation and contact with the reaction mass, but low enough such that carry over of reaction mass with the vapor stream leaving the reactor is insignificant. Generally, the velocity is such that the product of the vapor velocity in ft/sec times the square root of the vapor density in lbs/ft$^3$ is 0.2 to 1.5, preferably 0.5 to 1.0. The open area of the sieve trays may be 1 to 10% of the total area, preferably 3 to 5%, and the holes may be $\frac{1}{16}$ to $\frac{3}{8}$ inch in diameter, preferably $\frac{1}{8}$ to $\frac{1}{4}$ inch in diameter.

Typical sugar alcohols, in particular tetritols, pentitols and hexitols, are suitable for use in the process as starting materials. The starting materials may be sugar alcohols, monoanhydro sugar alcohols, or a mixture thereof. Particularly preferred starting materials include erythritol, threitol, xylitol, arabinitol, ribitol, glucitol (also known as D-sorbitol or sorbitol), D-mannitol (mannitol), galactitol and iditol. Sorbitol is most preferred because it is readily available and can be obtained on a large industrial scale by the reduction of glucose with hydrogen, and the resulting product, isosorbide, is especially valuable for use in the preparation of polyester polymers and copolymers. The preferred form of sorbitol is as an aqueous solution, about 45 wt %, before it is concentrated to the 70 wt % commercial product.

A "dilute" (i.e., substantially less than 70% by weight) aqueous solution is the preferred feed for economic reasons, since sugar alcohols are generally produced as an aqueous solution which is subsequently evaporated to obtain a concentrated solution, typically about 70% by weight sugar alcohol, or the sugar alcohols in solid form. Using the original dilute solution in the present invention thus eliminates a processing step.

Feeding to the reaction vessel a more concentrated sugar alcohol solution (e.g., 70%) and injecting a separate stream of liquid water or steam is equivalent to starting with the more dilute sugar alcohol stream according to the present invention. One can also use an inert gas stream (e.g., nitrogen or $CO_2$) to serve the same purpose as the water vapor, i.e., to transport the reaction mass through the multiple stages of the reaction vessel, and separate the product dianhydro sugar alcohols from the reaction mass.

The catalysts used to facilitate the dehydration reaction are typically strong acid catalysts. One class of acid catalyst that can be used includes soluble acids. Examples of such acid catalysts include sulfuric acid, phosphoric acid, p-toluene sulfonic acid, methanesulfonic acid and the like. Sulfuric acid is a preferred catalyst from this class.

Alternatively, acid anion exchange resins can also be used, such as sulfonated polystyrenes, for example, AG50W-X12 from BioRad or perfluorinated ion-exchange polymers, such as Nafion®, available from E. I. du Pont de Nemours and Company (Wilmington, Del.). Inorganic ion exchange materials can also be used, such as acidic zeolites. In particular, H-beta zeolite from Degussa (Frankfurt, Germany) can be used in the process disclosed herein.

For the process of the present invention, a soluble catalyst is preferred, and sulfuric acid is most preferred. In this most preferred mode, the sulfuric acid comprises 0.25 to 2.5 wt % of the reaction mass, preferably 0.5 to 1.5 wt %. The sulfuric acid is supplied to the reactor as an aqueous solution ranging from 10 to 97% sulfuric acid. The acid strength and the manner of acid injection are such that there is minimal detrimental by-product formation at the point of introduction. The acid catalyst can be injected along with the sugar alcohol feed stream or directly into the reaction vessel at the first stage.

The dehydration is performed at elevated temperatures between 100 and 180° C., preferably at temperatures between 115 and 160° C., and most preferably at temperatures between 120 and 145° C. The elevated temperature of the dehydration reaction promotes rapid dehydration of the starting materials. However, over-temperature or prolonged high-temperature operation promotes the formation of byproducts and the further conversion of the desired product to undesired secondary products over time. Therefore, it is desirable to remove the desired reaction product from the high temperature reaction mixture rapidly to protect it against further reaction or decomposition.

The dehydration is preferably performed under reduced pressure for effective removal of water and for volatilizing the product formed from the reaction mass. The pressure depends upon the reaction temperature, moles of water vapor available per mole of product, and the desired degree of product separation. For volatilizing most of the product formed, the pressure is generally 10 to 60 mm Hg, preferably 10 to 50 mm Hg, most preferably 15 to 25 mm Hg.

For manufacturing isosorbide (1,4:3,6-dianhydrosorbitol), the preferred feed stream is about 45–50% by weight of sorbitol in water. A 45 wt % solution of sorbitol will generate about 18 moles of water vapor (from the aqueous solution and the water of dehydration) per mole of isosorbide generated by the dehydration reaction (assuming 80% conversion of sorbitol to isosorbide). In the present invention, this large quantity of water vapor (up to 95% of the total vapor on a molar basis) will carry with it most of the isosorbide from the reaction mass as it is formed. Also, a subsequent separation step to remove the isosorbide from the reaction mass, for example by distillation, is eliminated. Degradation reactions caused by the prolonged exposure of the reaction mass to elevated temperatures are also minimized. In one embodiment of the process, the product can be further purified within the reactor by contacting it with a small liquid stream of isosorbide. This liquid isosorbide stream can be generated within the reactor by partial condensation from the vapor stream or by introducing a stream from subsequent purification steps.

A preferred process for the production of anhydro sugar alcohols is described below in relation to FIG. 1. The operating conditions described are for the case when the starting material is sorbitol and the product is isosorbide. As shown in FIG. 1, the dehydration takes place in the reaction vessel (50), which is fitted with sieve plates for multistage operation and equipped with heaters (51, 52, and 53). It is provided with supply lines for starting materials, such as the aqueous solution of sugar alcohol (1) and acid catalyst (20), as well as outlet lines for product vapor removal (2) and high boilers removal (12).

Any means of heating may be employed to maintain the reaction vessel at the desired temperature. Internal steam coils for heaters (52) and (53) for stages 2 and 3, respectively, are schematically illustrated in FIG. 1. For the first stage, where most of the heat must be supplied in order to evaporate most of the water, an external heat exchanger (51) is selected for ease of fabrication. This heater is preferably a steam, shell and tube, heat exchanger that circulates the reaction mass through it with thermosyphon action. This provides for effective heat transfer without a circulation pump. With such an external heater, the feed material and catalyst are supplied to the reactor via this heater via line (1—1) along with the recirculating stream.

The process of the present invention is preferably conducted in multiple stages. The number of stages is preferably at least 2 and more preferably 3 to 6. FIG. 1 illustrates the use of 3 stages, (61), (62), and (63), which are achieved with 2 sieve plates as shown.

Most of the water is evaporated in the first stage (61) by means of the external circulation heater (51). The water vapor carries the reaction mass to the second stage (62), where further dehydration takes place, and so on, to the third stage wherein the dehydration is essentially completed and most of the isosorbide generated gets transferred from the liquid reaction mass to the vapor phase. Under the reduced pressure of about 18 to 22 mm Hg and about 145° C. reaction temperature, the high boiling byproducts are not vaporized but are left as liquid in the third stage (63) and withdrawn via line 12.

Under the reaction conditions, the isosorbide product is about 50 times more volatile than the nearest high boiling component. Thus, the non-water component of the vapors leaving the third stage is about 98% isosorbide. The purity can be enhanced to about 99% isosorbide by contacting the vapors with a small amount of liquid isosorbide condensed internally from the vapors, using cooling coils (54) schematically shown in FIG. 1. The vapor-liquid contacting can be achieved using any appropriate device known in the art. Depicted schematically in FIG. 1 is a low pressure drop, about 2 mm Hg, structural packing (70). The vapor stream containing mostly water and isosorbide is taken out of the reactor via line 2. It can be recovered in a condensation device connected to a source of vacuum to maintain it at reduced pressure. The condensation device can be of any design known in the art. A direct contact spray condenser is preferred for reasons of low pressure drop.

The reactor of FIG. 1 is sized and flow rates are adjusted such that hold up time for the isosorbide reaction mass is 1 to 5 hours, preferably 2 to 3 hours, with the assumption that reaction temperatures are 130 to 150° C. and catalyst injection is at a rate equal to about 0.5 to 1% of the rate of sorbitol feed (on a water-free basis). In one preferred embodiment of the process, a gradually increasing temperature profile is maintained for optimizing isosorbide generation rate and yield; the temperature is about 125° C. in the first stage (61), 135° C. in the second stage (62), and 145° C. in the third stage (63).

EXAMPLE

Manufacture of Isosorbide at Nominal 15 to 16 Million lb/year (Size of Reactor Approximately 12 ft in Diameter by 15 ft in Height)

A stream of 45% by weight sorbitol (balance water) is introduced via inlet (1) at a rate of 8490 lb/hr. It contains 21 lb-moles of sorbitol and about 259 lb-moles of water. Aqueous sulfuric acid, 10% by weight, is injected via line (20) at a rate of 200 lb/hr in sufficient quantity to maintain sulfuric acid concentration at 0.5–0.6 wt % of the sorbitol feed (water-free basis). Heat input to stage heaters (51), (52), and (53) is adjusted to maintain the temperatures at 125, 135, and 145° C., respectively. Pressure in the head space above the third stage is maintained at about 18 to 20 mm Hg. The dehydration reaction through all the stages forms about 16.8 lb-moles of isosorbide (80% yield). 4.2 lb-moles of starting sorbitol go to byproducts comprising monoanhydro sorbitol derivatives, dimers, oligomeric and polymeric materials, and decomposition products. The total amount of water vapor produced from feed stream evaporation and the dehydration of sorbitol is about 312 lb-moles. Under the reaction conditions, about 80% of the isosorbide formed volatilizes in 98% purity into the water vapor. The bottoms are removed via line (12) at a rate of about 1110 lb/hr. Under these conditions, the hold up time is about 3 hours. The vapor stream, after contacting with about 10% internal reflux, is greater than 99% pure isosorbide (water-free basis) and leaves the reaction vessel via line (2) at 16 mm Hg pressure. It comprises 312 lb-moles/hr or 5616 lb/hr water vapor and 13.44 lb-moles/hr or 1962 lb/hr isosorbide. Upon condensation, it produces the nominal 15 to 16 million lb/year of isosorbide as about 25.9% aqueous solution. This may be concentrated or purified further depending on the intended use of the product.

What is claimed is:

1. A continuous process for the manufacture of dianhydro sugar alcohols comprising:
   (a) continuously feeding an aqueous solution comprising one or more sugar alcohols or monoanhydro sugar alcohols to a first stage of a multistage reaction vessel;
   (b) continuously heating the aqueous solution in the first stage in the presence of a dehydration catalyst to form a partially dehydrated reaction mass and water vapor;
   (c) simultaneously transporting the partially dehydrated reaction mass from the first stage upwards to one or more additional stages of the multistage reactor with water vapor from step (b) while further dehydrating the sugar alcohols to form dianhydro sugar alcohols and simultaneously removing from the reaction mass most of the dianhydro sugar alcohols formed;
   (d) continuously removing a vapor stream comprising water and dianhydro sugar alcohol product from the reaction vessel and recovering the dianhydrosugar alcohols; and
   (e) continuously removing high boiling by-products from the reaction vessel as a liquid stream from the final stage of the reaction vessel at a rate coordinated with the feed rate of the aqueous solution so as to maintain a nearly constant quantity of reaction mass in the multistage reaction vessel.

2. The process of claim 1 wherein the sugar alcohol is sorbitol and the product is isosorbide.

3. The process of claim 2 wherein the sorbitol feed is an about 45 to 50 weight % aqueous solution.

4. The process of claim 1 wherein the dehydration catalyst is sulfuric acid.

5. The process of claim 4 wherein the concentration of sulfuric acid is 0.25 to 2.5% by weight of the reaction mass.

6. The process of claim 1 conducted at a temperature of 110–180° C.

7. The process of claim 1 wherein the multistage reaction vessel is maintained at a pressure of 10 to 60 mm Hg.

8. The process of claim 7 wherein the multistage reaction vessel is maintained at a pressure from 15 to 25 mm Hg.

9. The process of claim 1 wherein the multistage reaction vessel has 2 to 6 stages.

10. The process of claim 9 wherein the multistage reaction vessel has 3 to 5 stages.

11. The process of claim 1 wherein the hold up time of the reaction mass in the multistage reaction vessel is 1 to 5 hours.

12. The process of claim 11 wherein the hold up time of the reaction mass in the vessel is 2 to 3 hours.

13. The process of claim 1 wherein the vapor stream is contacted with a liquid stream of product within the vessel.

14. The process of claim 13 wherein the liquid stream of product is obtained by partial internal condensation.

15. The process of claim 14 wherein low pressure drop structured packing is used for contacting the vapor stream and the liquid stream of product.

16. The process of claim 1 wherein the velocity of the vapor stream in ft/sec times the square root of the vapor density in lbs/ft$^3$ is from 0.2 to 1.5.

17. The process of claim 16 wherein the vapor velocity in ft/sec times the square root of the vapor density in lbs/ft$^3$ is from 0.5 to 1.0.

18. The process of claim 1 wherein the vapor stream is condensed in a low pressure drop, direct contact spray condenser.

19. The process of claim 1 further comprising product purification steps.

20. The process of claim 1 wherein the concentration of the sugar alcohol is 40 to 50% by weight.

* * * * *